(12) United States Patent
Park et al.

(10) Patent No.: US 9,974,822 B2
(45) Date of Patent: May 22, 2018

(54) COMPOSITION CONTAINING COMPOSITE EXTRACT OF REHMANNIA GLUTINOSA AND PUERARIA LOBATA FOR PREVENTING OR TREATING MENOPAUSAL SYMPTOMS

(71) Applicant: UNIVERSITY-INDUSTRY COOPERATION GROUP OF KYUNG HEE UNIVERSITY, Gyeonggi-do (KR)

(72) Inventors: Juyeon Park, Gyeonggi-do (KR); Sung Hyun Lee, Gyeonggi-do (KR); Mikyung Song, Seoul (KR); Aihong Kim, Gyeonggi-do (KR); Hocheol Kim, Seoul (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 0 days. days.

(21) Appl. No.: 14/897,617

(22) PCT Filed: Jun. 10, 2014

(86) PCT No.: PCT/KR2014/005059
§ 371 (c)(1),
(2) Date: Dec. 10, 2015

(87) PCT Pub. No.: WO2014/200234
PCT Pub. Date: Dec. 18, 2014

(65) Prior Publication Data
US 2016/0136217 A1    May 19, 2016

(30) Foreign Application Priority Data
Jun. 11, 2013  (KR) ........................ 10-2013-0066592

(51) Int. Cl.
*A61K 36/488* (2006.01)
*A61K 36/64* (2006.01)
*A61K 36/804* (2006.01)

(52) U.S. Cl.
CPC ............ *A61K 36/64* (2013.01); *A61K 36/488* (2013.01); *A61K 36/804* (2013.01); *A23V 2002/00* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 6,164,281 A * | 12/2000 | Zhao | A61K 31/07 128/898 |
| 7,482,029 B2 * | 1/2009 | Cohen | A61K 36/638 424/725 |
| 8,053,001 B2 * | 11/2011 | Kim | A61K 36/254 424/725 |
| 8,241,679 B2 | 8/2012 | Kim et al. | 424/728 |
| 2006/0222721 A1 | 10/2006 | Cohen | 424/741 |
| 2009/0068299 A1 | 3/2009 | Cohen | 424/757 |
| 2009/0186102 A1 | 7/2009 | Hwang et al. | 424/725 |
| 2010/0055213 A1 | 3/2010 | Kim et al. | 424/728 |
| 2010/0316741 A1 | 12/2010 | Kim et al. | 424/728 |
| 2016/0008414 A1 | 1/2016 | Kim et al. | 424/725 |

FOREIGN PATENT DOCUMENTS

| | | |
|---|---|---|
| JP | 2005-325107 | 11/2005 |
| KR | 10-0419121 | 2/2004 |
| KR | 10-2004-0038481 | 5/2004 |
| KR | 10-0853078 | 8/2008 |
| KR | 10-2013-0003520 | 1/2013 |

OTHER PUBLICATIONS

"Rhemannia Glutinosa" (http://www.chineseherbshealing.com/rehmannia-glutinosa/)—accessed Oct. 2016.*
Letter/Written Disclosure of the Information Disclosure Statement for the above-referenced application, mailed on Mar. 22, 2016, 2 pages.
English language abstract of JP 2005-325107, published Nov. 24, 2005, European Patent Office, 1 page.
English language abstract of KR 10-0419121 (Pub. No. 10-2004-0010176; App. No. 10-2003-0048109), published Feb. 18, 2004, European Patent Office, 1 page.
English language abstract of KR 10-0853078 (App. No. 10-2007-0029014), published Aug. 19, 2008, European Patent Office, 1 page.
English language abstract of KR 10-2004-0038481 (App. No. 10-2002-0067444), published May 8, 2004, Korean Intellectual Property Office, 1 page.
English language abstract of KR 10-2013-0003520 (App. No. 10-2011-0064928), published Jan. 9, 2013, Korean Intellectual Property Office, 1 page.
Kalin, M.F. & Zumoff, B., "Sex hormones and coronary disease: a review of the clinical studies." Steroids. 55:330-352 (1990).
Machine English translation of JP 2005-325107, published Nov. 24, 2005, Japan Patent Office, 19 pages.
Machine English translation of KR 10-0419121 (Pub. No. 10-2004-0010176; App. No. 10-2003-0048109), published Feb. 18, 2004, Korean Intellectual Property Office, 13 pages.

(Continued)

*Primary Examiner* — Susan Hoffman
(74) *Attorney, Agent, or Firm* — Rubin and Rudman LLP

(57) ABSTRACT

The present invention relates to a composition and functional health food containing a composite extract of *Rehmannia glutinosa* and *Pueraria lobata* for preventing or treating menopausal symptoms; and a method for preventing or treating menopausal symptoms by administering the composite extract. The composite extract of *Rehmannia glutinosa* and *Pueraria lobata* of the present invention can ameliorate weight increase, which is the representative symptom of menopausal women, and can effectively improve osteoporosis and blood cholesterol. Thus, the composition can be useful as a pharmaceutical composition or functional heath food for preventing or treating menopausal symptoms, and can be used in preventing or treating menopausal symptoms.

3 Claims, 2 Drawing Sheets

(56) References Cited

OTHER PUBLICATIONS

Machine English translation of KR 10-0853078 (App. No. 10-2007-0029014), published Aug. 19, 2008, Korean Intellectual Property Office, 11 pages.

Machine English translation of KR 10-2004-0038481 (App. No. 10-2002-0067444), published May 8, 2004, Korean Intellectual Property Office, 12 pages.

Machine English translation of KR 10-2013-0003520 (App. No. 10-2011-0064928), published Jan. 9, 2013, Korean Intellectual Properly Office, 27 pages.

Park et al., "Bone mineral density changes after ovariectomy in rats as an osteopenic model: stepwise description of double dorso-lateral approach," J Korean Neurosurg Soc, 48(4):309-312 (2010).

Writing Group for the Women's Health Initiative Investigators, "Risks and Benefits of Estrogen Plus Progestin in Healthy Postmenopausal Women," JAMA 288(3):321-333 (2002).

International Search Report and Written Opinion, dated Sep. 18, 2014, in connection with International Patent Application No. PCT/KR2014/005059 [English Translation], 12 pages.

International Preliminary Report on Patentability, dated Dec. 15, 2015, in connection with International Patent Application No. PCT/KR2014/005059 [English Translation], 10 pages.

U.S. Appl. No. 12/518,010, filed Jun. 5, 2009, 2010/0316741, Dec. 16, 2010.

U.S. Appl. No. 14/648,240, filed Sep. 11, 2015, 2016/0008414, Jan. 14, 2016.

U.S. Appl. No. 14/785,312, filed Oct. 16, 2015.

Letter/ Written Disclosure of the Supplemental Information Disclosure Statement for the above-referenced application, mailed on Mar. 16, 2017, 3 pages.

Wang et al., "Puerariae radix prevents bone loss in ovariectomized mice," J. Bone Miner. Metab. 21(5):268-275 (2003).

Yeo et al., "Effects of a multi-herbal extract on type 2 diabetes," Chin. Med. 6(1):10 (2011).

Extended European Search Report, dated Feb. 21, 2017, in connection with corresponding European Patent Application No. 14811666.8, 9 pages.

Letter/Written Disclosure of the Supplemental Information Disclosure Statement for the above-referenced application, filed herewith on Nov. 29, 2017, 2 pages.

Response, submitted Sep. 8, 2017, to Extended European Search Report, dated Feb. 21, 2017, in connection with European Patent Application No. 14811666.8, 12 pages.

\* cited by examiner

[FIG. 1]
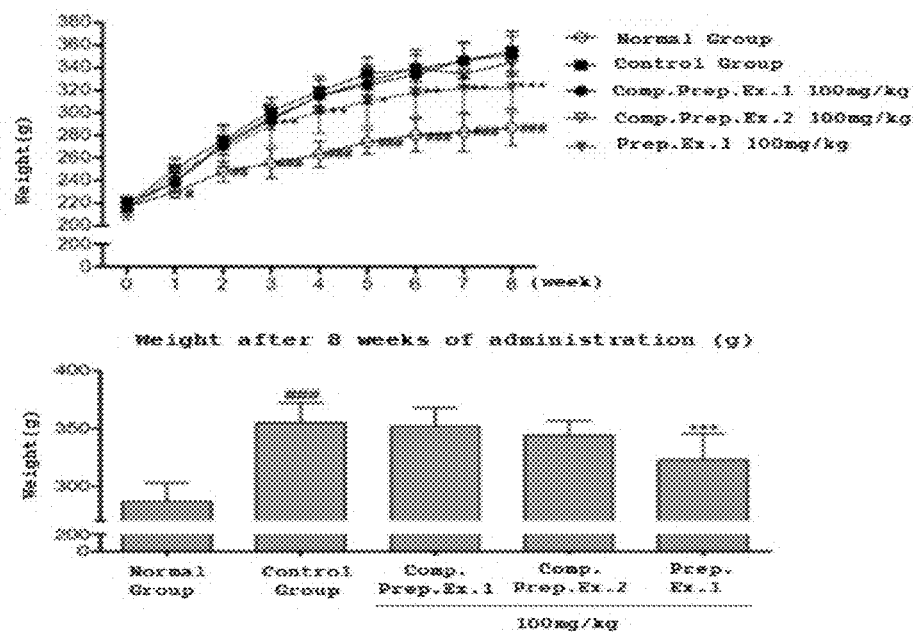
[FIG. 2]
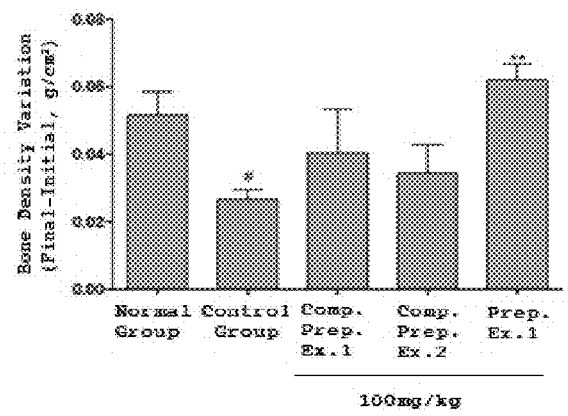

[FIG. 3]
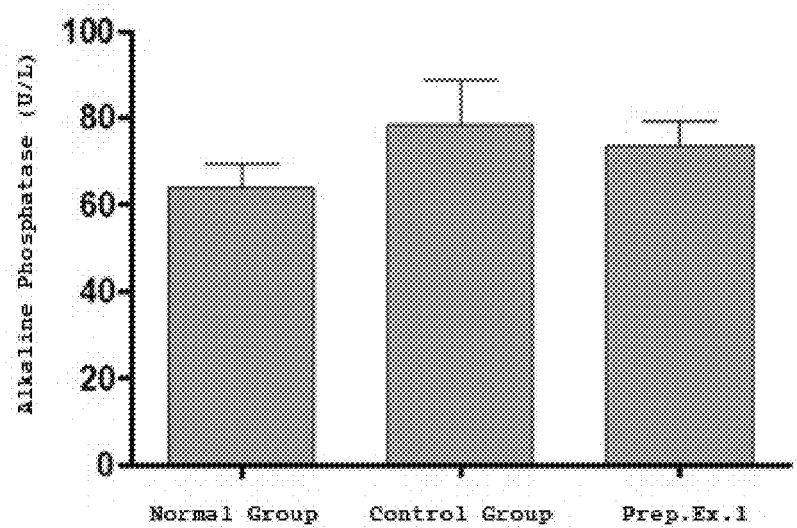
[FIG. 4]
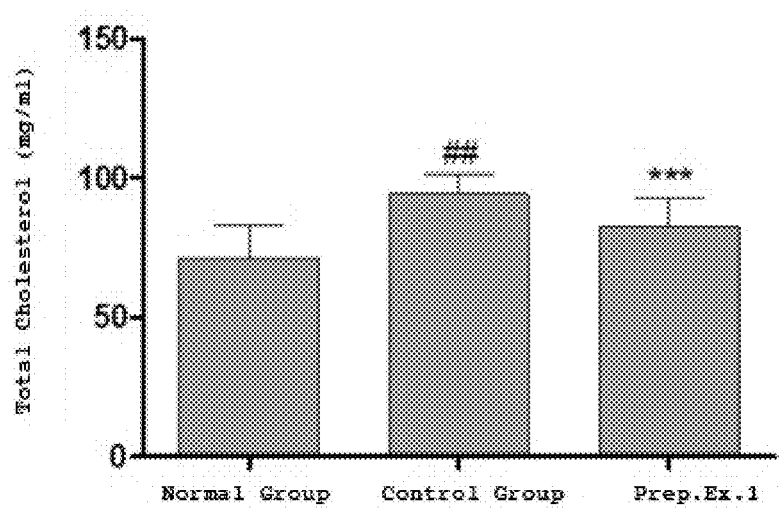

COMPOSITION CONTAINING COMPOSITE EXTRACT OF REHMANNIA GLUTINOSA AND PUERARIA LOBATA FOR PREVENTING OR TREATING MENOPAUSAL SYMPTOMS

RELATED APPLICATIONS

This application is the U.S. National Stage of International Application. No. PCT/KR2014/005059, filed 10 Jun. 2014, which claims benefit of priority to Korean Patent Application KR 10-2013-0066592, filed 11 Jun. 2013, the specification of which is incorporated by reference herein.

BACKGROUND OF THE INVENTION

1. Field of the Invention

The present disclosure relates to a pharmaceutical composition comprising a composite extract of *Rehmannia glutinosa* and *Pueraria lobata* for preventing or treating menopausal symptoms, and a method of preventing or treating menopausal symptoms.

2. Description of the Related Art

Population ratio of aged people over 65 in 2005 in Korea takes 9.1% and it is expected to become an aged society with more than 14% of population ratio in 2019. Also, average female life expectancy is 80.4 in 2002, thus particular attention on female's healthy life for 30 years after menopause is required.

The World Health Organization (WHO) defines menopause as it is an end of childbearing period because of termination of estrogen secretion due to ovarian failure, and transition period from adolescence to senescence. Generally, climacterium is a kind of endocrine symptoms and a transition period where physiological and sexual functions are being reduced or lost due to overall and gradual recession of ovarian function, and as a climacteric process, menopause, i.e. a permanent termination of menstruation that occurs after ovarian failure, comes succeedingly. Acute and chronic symptoms can be caused by decrease of estrogen production and hormonal changes such as increase of follicular stimulating hormone (FSH), luteininzing hormone (LH), etc. Postmenopausal women are encountered markedly increasing likelihood of psychologic and emotional symptoms, i.e. fatigue, agitation, insomnia, attention deficit, depression, amnesia, headache, anxiety, and nervousness or microcardia due to rapid decrease of estrogen, and likelihood of occurrence of fatigue and agitation according to sleep deprivation, occasional vertigo, paresthesia, palpitation and tachycardia, nausea, constipation, diarrhea, arthralgia, myalgia, cold hypersensitivity in hands and feet and weight increase, and uterus involution due to relapsing hot flush also markedly increase. In addition, osteoporosis can easily be induced and mortality increases due to cardiovascular diseases such as heart disease, hypertension and stroke (Kalin MF & Zumoff B. Steroids 55:330-352, 1990). Additionally, changes in skin and genitourinary system are incurred, and onset possibility of autoimmune diseases, cataract and colorectal cancer increases.

Furthermore, production of estrogen, (i.e. female hormone) rapidly decreases during menopausal period. There is a problem with climacteric women that cholesterol is easily accumulated in their blood vessel because estrogen functions as protecting blood vessel by decreasing cholesterol level through blocking accumulation of visceral fat. Recently, a research paper reported that onset possibility of cardiovascular diseases is higher for climacteric women compared to perimenopausal women in same age.

Hormone replacement therapy and treatment with NSAIDs and the like have been developed as therapies for improving menopausal symptoms, and the hormone replacement therapy that administers estrogen is known as the most effective method among the therapies. However, as disclosed in theses such as Risks and Benefits of Estrogen Plus Progestin in Healthy Postmenopausal Women (JAMA, Jul. 17, 2002-Wol 288, no3), it is known that hormone therapies using estrogen etc. may cause various risks. In detail, long-term use of the drugs according to said therapy could incur endometrial cancer, breast cancer, hypertension, thrombosis, biliary, urinary calculi, etc. and also, menstrual bleeding can be incurred, and a problem lies that drugs cannot be administered without doctor's prescription because of the side effects such as ovarian hyperstimulation and the like. To overcome such problem caused by the drug therapy, there are attempts to develop improving agents for female menopausal symptoms with natural crude drugs as active ingredients.

For example, Korean Patent No. 10-0419121 discloses a crude drug composition comprising *folium phyllostachyos*, *Angelica gigas* root, Cnidium rhizome, *Paeonia lactiflora* root, Atractylodes rhizome white, *Poria cocos*, Red *ginseng* and soybean extract as main ingredients for improving female menopause symptoms through action that increases female hormone (i.e. 17β-estradiol).

*Rehmannia glutinosa* is a steamed and dried root of medicinal plants belongs in the Scrophulariaceae family which is used as a medicinal ingredient in field of oriental medicine. It is known to have efficacy of treating chilling pain in waist and knee, dizziness, and blackening hair. It has been used for various chronic diseases including internal body heat due to feeble health condition, dry throat, thirst, etc. Iridoid glucosides such as catalpol, leonuride, aucubin, mielittoside, rehmannioside A, B, C and D; and saccharides such as stachyose, raffinose and sucrose are main ingredients of *Rehmannia glutinosa*. Moreover, it is reported that there are also mannitol and 10 types of amino acids other than the above.

*Radix Puerariae* is a root of kudzu vine (i.e. deciduous climbing plant) belongs to the Leguminosae family. *Radix Puerariae* has efficacy in alcohol poisoning recovery, diaphoresis treatment, macula treatment, thirst quenching, pus detoxication and treatment, and diarrhea treatment. Thus it has been frequently used for treating cold, emesis, measles, oligodipsia, diarrhea, angina pectoris, hypertension, migraine, retinal artery occlusion, sudden deafness, alcohol intoxication, etc. clinically. Active ingredients of *Radix Puerariae* include as flavonoids such as daidzin, daidzein, puerarin and puerarin xyloside; and a large volume of starches.

However, no studies on the composite extract of *Rehmannia glutinosa* and *Pueraria lobata* are reported so far. Consequently, the present inventors completed the present disclosure upon confirmation that the composite extract can improve weight increase which is a menopausal symptom, and decrease blood cholesterol and serum alkaline phosphatase while studying on effects of the composite extract of *Rehmannia glutinosa* and *Pueraria lobata*.

SUMMARY OF THE INVENTION

It is an object of the present disclosure to provide the pharmaceutical composition comprising composite extract of *Rehmannia glutinosa* and *Pueraria lobata* as an active ingredient for preventing or treating menopausal symptoms.

The other object of the present disclosure is to provide a functional health food comprising the composite extract of *Rehmannia glutinosa* and *Pueraria lobata* as an active ingredient for preventing or improving menopausal symptoms.

Another object of the present disclosure is to provide a method for preventing or treating menopausal symptoms comprising administrating the composite extract of *Rehmannia glutinosa* and *Pueraria lobata* to a subject.

To achieve the above object, the present disclosure provides the pharmaceutical composition comprising the composite extract of *Rehmannia glutinosa* and *Pueraria lobata* as an active ingredient for preventing or treating menopausal symptoms.

Additionally, the present disclosure provides the pharmaceutical composition for preventing or treating menopausal symptoms wherein the composite extract is extracted with water or alcohol as an extraction solvent.

In addition, the present disclosure provides the pharmaceutical composition for preventing or treating menopausal symptoms wherein the composite extract inhibits weight increase of climacteric women.

Furthermore, the present disclosure provides the pharmaceutical composition for preventing or treating menopausal symptoms wherein the composite extract increases bone density of climacteric women.

Moreover, the present disclosure provides the pharmaceutical composition for preventing or treating menopausal symptoms wherein the composite extract decreases serum alkaline phosphatase of climacteric women.

Also, the present disclosure provides the pharmaceutical composition for preventing or treating menopausal symptoms wherein the composite extract decreases cholesterol of climacteric women.

Furthermore, the present disclosure provides the pharmaceutical composition for preventing or treating menopausal symptoms wherein extracts of *Rehmannia glutinosa* and *Pueraria lobata* are mixed in weight ratio of 1:3-1:5.

Furthermore, the present disclosure provides the functional health food for preventing or improving menopausal symptoms comprising the composite extract of *Rehmannia glutinosa* and *Pueraria lobata* as an active ingredient.

Furthermore, the present disclosure provides the functional health food for preventing or treating menopausal symptoms wherein extracts of *Rehmannia glutinosa* and *Pueraria lobata* are mixed in weight ratio of 1:3-1:5.

Furthermore, the present disclosure provides the method for preventing or treating menopausal symptoms comprising administering the composite extract of *Rehmannia glutinosa* and *Pueraria lobata* to a subject.

Furthermore, the present disclosure provides the method for preventing or treating menopausal symptoms wherein the composite extract is extracted with water or alcohol as an extraction solvent.

Furthermore, the present disclosure provides the method for preventing or treating menopausal symptoms wherein extracts of *Rehmannia glutinosa* and *Pueraria lobata* are mixed in weight ratio of 1:3-1:5.

Advantageous Effect

The composite extract of *Rehmannia glutinosa* and *Pueraria lobata* of the present disclosure can be utilized as a pharmaceutical composition or a functional health food for preventing or improving menopausal symptoms, and can be used for preventing or treating menopausal symptoms because the composite extract of *Rehmannia glutinosa* and *Pueraria lobata* of the present disclosure can improve weight increase which is a major symptom of climacteric women, and can effectively ameliorate osteoporosis and blood cholesterol.

BRIEF DESCRIPTION OF THE DRAWINGS

FIG. 1 shows weight variation in female menopause induction model upon oral administration of 100 mg/kg of a single extract of *Rehmannia glutinosa* (Comparative Preparational Example 1), a single extract of *Pueraria lobata* (Comparative Preparational Example 2) and the composite extract of *Rehmannia glutinosa* and *Pueraria lobata* (Preparational Example 1).

FIG. 2 shows bone density variation in female menopause induction model upon oral administration of 100 mg/kg of the single extract of *Rehmannia glutinosa* (Comparative Preparational Example 1), the single extract of *Pueraria lobata* (Comparative Preparational Example 2) and the composite extract of *Rehmannia glutinosa* and *Pueraria lobata* (Preparational Example 1).

FIG. 3 shows content variation of serum alkaline phosphatase in female menopause induction model upon oral administration of 100 mg/kg of the composite extract of *Rehmannia glutinosa* and *Pueraria lobata* (Preparational Example 1).

FIG. 4 shows total cholesterol decreasing effect in female menopause induction model upon oral administration of 100 mg/kg of the composite extract of *Rehmannia glutinosa* and *Pueraria lobata* (Preparational Example 1).

DESCRIPTION OF THE PREFERRED EMBODIMENTS

The present disclosure provides the pharmaceutical composition comprising the composite extract of *Rehmannia glutinosa* and *Pueraria lobata* as an active ingredient for preventing or treating menopausal symptoms.

The composite extract of *Rehmannia glutinosa* and *Pueraria lobata* of the present disclosure can be used as a pharmaceutical composition or a functional health food for preventing or improving menopausal symptoms because the said composite extract can improve weight increase and decrease blood cholesterol and serum alkaline phosphatase and accordingly, it can effectively ameliorate complex symptoms that can be incurred in climacteric women including weight increase, cholesterol increase, osteoporosis, etc.

The composite extract can be an extract extracted by using water, alcohol or mixed solvent thereof as an extraction solvent, and preferably, the alcohol can be $C_1$-$C_4$ lower alcohol.

The composite extract can ameliorate various symptoms of climacteric women such as fatigue, agitation, insomnia, attention deficit, depression, amnesia, headache and anxiety; nervousness or microcardia, occasional vertigo, paresthesia, heart palpitation, tachycardia, nausea, constipation, diarrhea, arthralgia, myalgia, cold hypersensitivity in hands and feet; and cardiovascular diseases such as weight increase, uterus involution, osteoporosis, heart disease, hypertension, stroke, etc., and specifically, the composite extract can have effects of ameliorating weight increase, increasing bone density, improving osteoporosis by decreasing serum alkaline phosphatase and decreasing cholesterol apropos of climacteric women.

The composite extract can be prepared by mixing extracts of *Rehmannia glutinosa* and *Pueraria lobata* in weight ratio of 1:1-1:5, preferably 1:3-1:5, and more preferably 1:3.

The composite extract of *Rehmannia glutinosa* and *Pueraria lobata* of the present disclosure can include both composition prepared by mixing each extract of *Rehmannia glutinosa* and *Pueraria lobata* and composition prepared by extracting mixture of *Rehmannia glutinosa* and *Pueraria lobata*.

The composite extract of *Rehmannia glutinosa* and *Pueraria lobata* is preferred to be prepared by a method comprising following steps but not limited to it:

(1) drying and crushing *Rehmannia glutinosa* and *Pueraria lobata*;

(2) extracting extracts by adding an extraction solvent to the crushed *Rehmannia glutinosa* and *Pueraria lobata*;

(3) cooling the extracts and filtering; and (4) concentrating the filtered extracts under reduced pressure and drying the same.

The *Rehmannia glutinosa* and *Pueraria lobata* in step (1) can be obtained without restriction. It could be cultivated, purchased or obtained by any other routes.

The extraction in step (2) can be shaking extraction, Soxhlet extraction or reflux extraction but not limited to these. It is preferable for extraction temperature to be 50-120° C. and more preferably to be 80-100° C. Additionally, it is preferable for extracting duration to be 2-24 hours, and extracting time to be 1-5 times.

The extraction solvent in step (2) can be water, alcohol or its mixture. It is preferable that the alcohol is $C_1$-$C_4$ lower alcohol and most preferably to use methanol or ethanol when the solvent is alcohol. In addition, it is preferable to add 5-15 times weight or volume of the extraction solvent compared to weight or volume of the *Rehmannia glutinosa* and *Pueraria lobata* in step (1), and it is more preferable to extract by adding 10 times weight or volume of the extraction solvent.

In step (4), a vacuum evaporator or a rotary vacuum evaporator is preferred to use for the concentration under reduced pressure; and drying under reduced pressure, drying in vacuo, boiling drying, spray drying or freeze drying is preferred for the drying in step (4) but not limited to the above.

The composition of the present disclosure can be administered in various forms of preparation such as oral or parenteral administration in case of actual clinical administration. Common diluents such as filler, extender, binder, humectants, disintegrant, surfactant, etc. or additives can be used for formulation of the composition.

Solid preparations for oral administration include tablets, pills, powders, granules and capsules, and these solid preparations can be manufactured by mixing at least one or more additives such as starch, calcium carbonate, sucrose, lactose, gelatin, etc. with the pharmaceutical composition of the present disclosure. Also, lubricant such as magnesium, stearate, talc, etc. can be used as well as simple additives.

Liquid preparations for oral administration include suspensions, liquid for internal use, emulsions, syrups, etc. but various additives such as humectants, sweetening agents, aromatic agents, preservatives and the like can be included as well as commonly used simple diluents such as water and liquid paraffin.

Preparations for parenteral administration include sterile aqueous solution, nonaqueous solvent, suspensions, emulsions, lyophilizer and suppository. Vegetable oils such as propylene glycol, polyethylene, glycol, etc., and injectable esters such as ethyl oleate, etc. can be used as the nonaqueous solvent and the suspensions. Base of the suppository can be witepsol, macrogol, tween 61, cacao butter, laurinum, glycerol, gelatin, etc. The pharmaceutical composition of the present disclosure can be administered by subcutaneous injection, intravenous injection or intramuscular injection when applying parenteral administration.

Dosage of the pharmaceutical composition of the present disclosure varies by degree of disease, form of drug, route of administration and duration of administration. It can be selected by those skilled in the art pro re nata. However, administering 0.1-1000 mg/kg of the extract of the present disclosure per a day is preferable to achieve desired effects. Administration can be once a day or divided into several times per a day. However, the said dosage explained hereinbefore does not limit scope of the present disclosure.

The composition of the present disclosure can be used solely or jointly with operation, hormone therapy, chemotherapy and methods using biological response modifiers for preventing or treating menopausal symptoms.

In addition, the present disclosure provides the functional health food comprising the composite extract of *Rehmannia glutinosa* and *Pueraria lobata* as an active ingredient for preventing or improving menopausal symptoms.

The functional health food of the present disclosure can be used by adding the composite extract of *Rehmannia glutinosa* and *Pueraria lobata* thereto intactly or with other foods or food ingredients. It can be adequately used in the usual manner. Content of active ingredients can be decided properly according to its purpose of use (e.g. prevention, health or therapeutical treatment). In general, 0.01-15.0 wt % of the composite extract of the present disclosure based on total food weight can be added when manufacturing foods or beverages.

Furthermore, types of food are not limited. Beverages, gums, vitamin complexes, drinks, etc. are examples of the foods whereto the composite extract of the present disclosure can be added. The foods include all kinds of health food in the conventional sense.

The functional health food of the present disclosure can be functional health beverages and the beverages can contain various flavoring agents or natural carbohydrates as additional ingredients like other beverages. The natural carbohydrates can be: monosaccharides such as glucose, fructose and the like; disaccharides such as maltose, sucrose, etc.; polysaccharides such as general sugars (e.g. dextrin and cyclodextrin) and the like; and sugar alcohols such as xylitol, sorbitol, erythritol, etc. Additionally, another flavoring agents (e.g. saccharin, aspartame, etc.) can be also used other than the above.

The functional health food of the present disclosure can contain various nutritional supplements, vitamins, minerals (i.e. electrolyte), flavoring agents such as synthetic flavoring agents and natural flavoring agents, coloring agents, enhancer (cheese, chocolate, etc.), pectic acids and its salt, alginic acid and its salt, organic acids, protective colloid thickener, pH modifier, stabilizer, preservatives, glycerin, alcohols and carbonator for carbonated beverages and the like.

Additionally, the present disclosure provides the method for preventing or treating menopausal symptoms comprising administering of the composite extract of *Rehmannia glutinosa* and *Pueraria lobata* to a subject.

Effective amount of the composite extract for preventing or treating menopausal symptoms can be administered when administering the composite extract to a subject. Menopausal symptoms that can be prevented or treated by administering the composite extract can be various symptoms of climacteric women including fatigue, agitation, insomnia, attention deficit, depression, amnesia, headache, anxiety; nervousness or microcardia, occasional vertigo, paresthesia, palpitation, tachycardia, nausea, constipation, diarrhea, arthralgia, myalgia, cold hypersensitivity in hands and feet; and cardiovascular diseases such as weight increase, uterus involution, osteoporosis, heart disease, hypertension, stroke, etc., and specifically, it can be weight increase, bone density decrease, serum alkaline phosphatase decrease and osteoporosis.

The subjects are directed to animals and typically those are mammals by which helpful effects can be exhibited through a treatment using the composite extract of the present disclosure. Primates such as human beings are preferred example of the subjects. Also, these subjects include every subject that already has or has a risk of having menopausal symptoms such as weight increase, bone density decrease, osteoporosis, cholesterol increase, etc.

The effective amount for preventing or treating menopausal symptoms is single dose or multiple doses. It is directed to an amount that provides desired results or subjective or objective advantages via sole use or combined use with one or more other compositions (i.e. other therapeutic agents for menopausal symptoms, etc.).

The composite extract can be an extract extracted by using water, alcohol or mixed solvent thereof as an extraction solvent, and preferably, the alcohol can be $C_1$-$C_4$ lower alcohol.

The composite extract can be prepared by mixing extracts of *Rehmannia glutinosa* and *Pueraria lobata* in weight ratio of 1:1-1:5, preferably 1:3-1:5, and more preferably 1:3.

The composite extract of *Rehmannia glutinosa* and *Pueraria lobata* of the present disclosure can include both composition prepared by mixing each extract of *Rehmannia glutinosa* and *Pueraria lobata* and composition prepared by extracting mixture of *Rehmannia glutinosa* and *Pueraria lobata*.

In addition, the present disclosure provides a use the composite extract of *Rehmannia glutinosa* and *Pueraria lobata* as preventive or therapeutic agent for preventing or treating menopausal symptoms.

Furthermore, the present disclosure provides a use of the composite extract of *Rehmannia glutinosa* and *Pueraria lobata* for the manufacture of therapeutic agents for preventing or treating menopausal symptoms.

The present disclosure will be described more fully hereinafter with reference to the accompanying Examples. However, the present disclosure may be embodied in many different forms, and should not be construed as being limited to the embodiments set forth herein.

EXAMPLE

Preparational Example 1: Preparation of the Composite Extract of *Rehmannia glutinosa* and *Pueraria Lobata*

The composite extract of *Rehmannia glutinosa* and *Pueraria lobata* was prepared by preparing and mixing each extract of *Rehmannia glutinosa* and *Pueraria lobata*. More specifically, powdered single extracts of *Rehmannia glutinosa* and *Pueraria lobata* were prepared by: adding 10 times weight of water to each 100 g of *Rehmannia glutinosa* (Yaksudang, China) and *Pueraria lobata* (Yaksudang, China) which were cut into small pieces; extracting twice repeatedly for 3 hours at 100° C. and filtering the extracts (150 mm diameter, 100 circle); concentrating the filtrate under reduced pressure to 60 brix; and lyophilizing the same (−80° C., 20 mmtorr). Succeedingly the composite extract was prepared by mixing the prepared single extracts of *Rehmannia glutinosa* and *Pueraria lobata* in the ratio stated in Table 1 below.

TABLE 1

| | | Rehmannia glutinosa Extract | Pueraria lobata Extract |
|---|---|---|---|
| Preparational Example 1 | Weight (g) | 2.5 | 7.5 |
| | Weight Ratio | 1 | 3 |

Comparative Preparational Examples 1 and 2: Preparation of the Single Extracts of *Rehmannia glutinosa* and *Pueraria lobata*

Single extracts of *Rehmannia glutinosa* and *Pueraria Lobata* were prepared by using *Rehmannia glutinosa* or *Pueraria Lobata* having weight stated in Table 2 below. Single extracts were prepared by adding 10 times weight of water to *Rehmannia glutinosa* or *Pueraria lobata* and extracting twice repeatedly in 3 hours at 100° C. 53.86 g of powdered *Rehmannia glutinosa* extract (Yield Rate: 53.86%) and 54.19 g of powdered *Pueraria lobata* (Yield Rate: 54.19%) were prepared by concentrating filtrates of the single extracts of *Rehmannia glutinosa* and *Pueraria lobata* under reduced pressure to 40 brix and lyophilizing the same.

TABLE 2

| | Weight (g) | Rehmannia glutinosa Extract | Pueraria lobata Extract |
|---|---|---|---|
| Comparative Preparational Example 1 | Single Extract of *Rehmannia glutinosa* | 10 | 0 |
| Comparative Preparational Example 2 | Single Extract of *Pueraria lobata* | 0 | 10 |

Example 1: Confirmation of Improving Effects of the Composite Extract on Menopausal Symptoms <1-1> Preparation of Female Menopausal Disorder-Induced Animal Model 8-week old female rats (Sprague-Dawley, Samtako Bio Korea Inc.) were purchased and received sufficient food and water to be adapted to an experimental environment. Every experimental animal was housed for a week and anesthetized by using isoflurane. Ovariectomy (OVX) that is conducted by removing ovary via excising subcostal area and resuturing the excised area (Bone mineral density changes after ovariectomy in rats as an osteopenic model: stepwise description of double dorso-lateral approach, J Korean Neurosurg Soc. 2010 October; 48(4):309-12) was performed and accordingly, the model in which menopausal disorder caused by estrogen deficiency was prepared.

<1-2> Weight-Reducing Effect of the Composite Extract

Weight-reducing effect was observed to see improving effect of the composite extract of *Rehmannia glutinosa* and *Pueraria lobata* on menopausal symptoms by administering the composite extract of Preparational Example 1 and the single extracts of Comparative Preparation Examples 1 and 2 to the rats in the menopausal disorder-induced model. The menopausal disorder-induced rat model prepared in <1-1> whereto double distilled water was orally administered was set as a normal group and rats whereto double distilled water was orally administered after ovariectomy were set as a control group. 100 mg/kg of the single extracts of *Rehmannia glutinosa* and *Pueraria lobata* and the composite extract of *Rehmannia glutinosa* and *Pueraria lobata* were orally administered to the menopausal disorder-induced rat model as an experimental group. Distilled water, the single extracts of *Rehmannia glutinosa* and *Pueraria lobata* and the composite extract of *Rehmannia glutinosa* and *Pueraria lobata* were orally administered twice a day for 8 weeks and measured rats' weight once a day. 22±2° C. of temperature and 50±10% of relative humidity were maintained and lighting cycle was controlled (07:00 light on-19:00 light off) by fluorescent lights. Weight of each rat was measured after termination of the 8-week experiment.

Result is illustrated in FIG. 1.

As illustrated in FIG. 1, apropos of the rats whereto the composite extract of *Rehmannia glutinosa* and *Pueraria lobata* (Preparation Example 1) was administered, significant weight-reducing effect compared to the control group was shown after 3 weeks from the ovariectomy, and it was observed that the weight loss was as significant as 9.1% after 8 weeks where weight of the rats were 322.7±22.5 g compared to 354.8±17.5 g of weight of the control group (P<0.001). However, weights of the single extract of *Rehmannia glutinosa*-administered group (Comparative Preparation Example 1) and the single extract of *Pueraria lobata*-administered group (Comparative Preparation Example 2) were respectively 351.6±16.5 g and 344.6±11.9 g after 8 weeks. These were each 2.9% and 0.9% of weight loss compared to 354.8±17.5 g of weight of the control group and accordingly, it was confirmed that these groups do not exhibit significant weight-reducing effects.

<1-3> Bone Density Increasing Effect of the Composite Extract

Variation between initial bone density and bone density after 8 weeks was observed to see improving effect of the composite extract of *Rehmannia glutinosa* and *Pueraria lobata* on menopausal symptoms by orally administering 100 mg/kg of the composite extract of Preparational Example 1 and the single extracts of Comparative Preparation Examples 1 and 2 to the menopausal disorder-induced rat model prepared in Example <1-1>. Bone density was measured by using PIXImus densitometer (GE LUNAR Co., #30983).

Result is shown in FIG. 2.

As shown in FIG. 2, apropos of the rats whereto the composite extract of *Rehmannia glutinosa* and *Pueraria lobata* (Preparation Example 1) was administered, bone density variation after 8 weeks was observed as 0.062±0.015 g/cm$^2$ which was highly significant bone density increment by 56.9% compared to 0.027±0.005 g/cm$^2$ of the control group (P<0.005). However, bone density variations of the single extract of *Rehmannia glutinosa*-administered group (Comparative Preparation Example 1) and the single extract of *Pueraria lobata*-administered group (Comparative Preparation Example 2) after 8 weeks were 0.040±0.013 g/cm$^2$ and 0.034±0.019 g/cm$^2$ respectively and accordingly, it was confirmed that these groups do not exhibit significant effects when comparing with 0.027±0.005 g/cm$^2$ of the control group.

<1-4> Measurement of Serum Alkaline Phosphatase (ALP) Content of the Composite Extract Serum alkaline phosphatase (ALP) content that could be an indicator of osteoporosis improvement was measured to confirm whether the composite extract of *Rehmannia glutinosa* and *Pueraria lobata* is effective for osteoporosis which is one of the menopausal symptoms by orally administering 100 mg/kg of the composite extract of *Rehmannia glutinosa* and *Pueraria lobata* to the menopausal disorder-induced rat model. Serum alkaline phosphatase was measured by using VetTest (IDEXX Lab Inc, USA).

Result is shown in FIG. 3.

As shown in FIG. 3, after 8 weeks, alkaline phosphatase of the rats whereto the composite extract of *Rehmannia glutinosa* and *Pueraria lobata* (Preparation Example 1) was administered was 73.7±5.7 mU/L and it was observed that alkaline phosphatase was 6.3% reduced compared to 78.4±10.6 mU/L of the control group. Therefore, it was confirmed that the composite extract of *Rehmannia glutinosa* and *Pueraria lobata* has effects of reducing alkaline phosphatase value which is increased when having osteoporosis that is one of the menopausal symptoms.

<1-5> Effects of the Composite Extract on Total Cholesterol

To confirm effects of the composite extract on total cholesterol in serum, 100 mg/kg of the composite extract of Preparation Example 1 was orally administered to the menopausal disorder-induced model prepared in Example <1-1> and laparotomy was performed on the rats after 8 weeks after anesthetizing the rats by using isoflurane. Blood was collected from abdominal artery and serum was separated. Serum was analyzed by using VetTest (IDEXX Lab Inc, USA).

Result is shown in FIG. 4.

As shown in FIG. 4, after 8 weeks, total cholesterol of the rats whereto the composite extract of *Rehmannia glutinosa* and *Pueraria lobata* (Preparation Example 1) was administered was 82.8±10.2 mg/ml and 13.9% of significant total cholesterol decrease compared to 94.4±6.8 mg/ml of the control group was observed (P<0.001). Accordingly, it was confirmed that the composite extract of *Rehmannia glutinosa* and *Pueraria lobata* can effectively decrease blood cholesterol which is one of the menopausal symptoms.

Formulation Example 1: Preparation of Medicaments

<1-1> Preparation of Powders

| | |
|---|---|
| Composite extract of *Rehmannia glutinosa* and *Pueraria lobata* | 100 mg |
| Lactose | 100 mg |
| Talc | 10 mg |

Powders can be prepared by mixing the ingredients and filling a sealed bag with the same.

<1-2> Preparation of Tablets

| | |
|---|---|
| Composite extract of *Rehmannia glutinosa* and *Pueraria lobata* | 100 mg |
| Corn starch | 100 mg |
| Lactose | 100 mg |
| Magnesium stearate | 2 mg |

Tablets can be prepared by mixing the ingredients and tableting in the usual manner as common tablet preparations.

<1-3> Preparation of Capsules

| | |
|---|---|
| Composite extract of *Rehmannia glutinosa* and *Pueraria lobata* | 100 mg |
| Corn starch | 100 mg |
| Lactose | 100 mg |
| Magnesium stearate | 2 mg |

Capsules can be prepared by mixing the ingredients in the usual manner as common capsule preparations and filling gelatin capsules with the same.

<1-4> Preparation of Injections

| | |
|---|---|
| Composite extract of *Rehmannia glutinosa* and *Pueraria lobata* | 100 mg |
| Sterile distilled water for injection | q.s |
| pH modifier | q.s |

Injections can be prepared in the usual manner as common injection preparations to have the ingredient contents stated above per 1 ampoule (2 ml).

<1-5> Preparation of Solutions

| | |
|---|---|
| Composite extract of *Rehmannia glutinosa* and *Pueraria lobata* | 100 mg |
| Sugar | 20 g |
| Isomerose | 20 g |
| Lemon flavor | q.s |

Total amount was adjusted to be 1.00 ml by adding purified water. Solutions can be prepared by mixing the ingredients in the usual manner as common solution preparations, filling a brown-colored bottle with the mixed ingredients and sterilizing the same.

Formulation Example 2: Preparation of the Functional Health Food

| | |
|---|---|
| Composite extract of *Rehmannia glutinosa* and *Pueraria lobata* | 100 mg |
| Vitamin mixture | q.s |
| Vitamin A acetate | 70 |
| Vitamin E | 1.0 |
| Vitamin B1 | 0.13 |
| Vitamin B2 | 0.15 |
| Vitamin B6 | 0.5 |
| Vitamin B12 | 0.2 |
| Vitamin C | 10 |
| Biotin | 10 |
| Nicotinic acid amide | 1.7 |
| Folate | 50 |
| Calcium pantothenate | 0.5 |
| Mineral mixture | q.s |
| Ferrous sulfate | 1.75 |
| Zinc oxide | 0.82 |
| Magnesium carbonate | 25.3 |
| Monopotassium phosphate | 15 |
| Dipotassium phosphate | 55 |
| Potassium citrate | 90 |
| Potassium carbonate | 100 |
| Magnesium chloride | 24.8 |

Composition ratio of the vitamins and the mineral mixture was composed of relatively adequate ingredients for the functional health food as a preferred embodiment. However, a mixing ratio may be embodied in many different forms, and the ingredients can be used for preparation of functional health food compositions (e.g. healthy candies, etc.) in the usual manner by mixing the ingredients in the usual manner as common functional health food preparations.

Formulation Example 3: Preparation of the Functional Health Beverages

| | |
|---|---|
| Composite extract of *Rehmannia glutinosa* and *Pueraria lobata* | 100 mg |
| Citric acid | 1000 |
| Oligosaccharides | 100 g |
| Plum extracts | 2 g |
| Taurine | 1 g |
| Total amount including purified water | 900 |

The ingredients can be used for preparing the functional health beverages of the present disclosure by mixing the ingredients in the usual manner as common functional health beverage preparations, stir heating at 85° C. for an hour, filtering the prepared solution and seal sterilizing the obtained filtrates in a 2 l container, and keeping the same refrigerated.

The composition ratio was composed of relatively adequate ingredients for the functional health beverages as a preferred embodiment. However, a mixing ratio may be embodied in many different forms in consideration of regional and cultural preferences such as consumers, countries, purpose of use, etc.

INDUSTRIAL APPLICABILITY

The composite extract of *Rehmannia glutinosa* and *Pueraria lobata* of the present disclosure can ameliorate weight increase that is a representative menopausal symptom, and effectively improve osteoporosis and blood cholesterol. Therefore the composite extract can be used usefully as a pharmaceutical composition or a functional health food for preventing or improving menopausal symptoms.

What is claimed is:

1. A method for preventing or treating menopausal symptoms, comprising administering a composite extract of *Rehmannia glutinosa* and *Pueraria lobata* to a subject, wherein:
the *Rehmannia glutinosa* is a steamed and dried root of a medicinal plant belonging to the Scrophulariaceae family, and
the composite extract inhibits weight increase, increases bone density, reduces serum alkaline phosphatase and reduces cholesterol.

2. The method for preventing or treating menopausal symptoms according to claim 1, wherein the composite extract is extracted with water or alcohol as the extraction solvent.

3. The method for preventing or treating menopausal symptoms according to claim 1, wherein the composite extract comprises extracts of *Rehmannia glutinosa* and *Pueraria lobata* mixed in a weight ratio of 1:3-1:5.

* * * * *